(12) United States Patent
Sterk

(10) Patent No.: US 6,756,371 B1
(45) Date of Patent: Jun. 29, 2004

(54) PHTHALAZINONE DERIVATIVES AS PDE4 INHIBITORS

(75) Inventor: Geert Jan Sterk, Utrecht (NL)

(73) Assignee: Altana Pharma AG, Constance (DE)

( * ) Notice: Subject to any disclaimer, the term of this patent is extended or adjusted under 35 U.S.C. 154(b) by 43 days.

(21) Appl. No.: 10/110,460

(22) PCT Filed: Oct. 24, 2000

(86) PCT No.: PCT/EP00/10446

§ 371 (c)(1),
(2), (4) Date: Apr. 12, 2002

(87) PCT Pub. No.: WO01/30766

PCT Pub. Date: May 3, 2001

(30) Foreign Application Priority Data

Oct. 25, 1999 (EP) .............................................. 99121242

(51) Int. Cl.$^7$ .................... C07D 413/10; C07D 413/12; C07D 417/12; A61K 31/5377; A61K 31/541
(52) U.S. Cl. ................. 514/228.2; 514/234.5; 544/6; 544/61; 544/70; 544/116
(58) Field of Search ................. 544/6, 61, 70, 544/116; 514/228.2, 234.5

(56) References Cited

U.S. PATENT DOCUMENTS

| | | | |
|---|---|---|---|
| 6,103,718 A | 8/2000 | Sterk | 514/239.3 |
| 6,255,303 B1 | 7/2001 | Sterk et al. | 514/222.5 |
| 6,380,196 B1 | 4/2002 | Ulrich et al. | 514/245 |

FOREIGN PATENT DOCUMENTS

| | | |
|---|---|---|
| EP | 0 763 534 | 3/1997 |
| WO | 94/12461 | 6/1994 |
| WO | 99/31071 | 6/1999 |

OTHER PUBLICATIONS

Montana, J.G. et al, Ann. Reports Med. Chem., vol. 36, 2001, pp. 41–56.*

* cited by examiner

*Primary Examiner*—Mukund J. Shah
*Assistant Examiner*—Thomas McKenzie
(74) *Attorney, Agent, or Firm*—Nath & Associates PLLC; Todd L. Juneau; Sheldon M. McGee

(57) ABSTRACT

The compounds of formula (I) in which R1, R2, A, B and Ar have the meanings as given in the description are novel effective PDe4 inhibitors

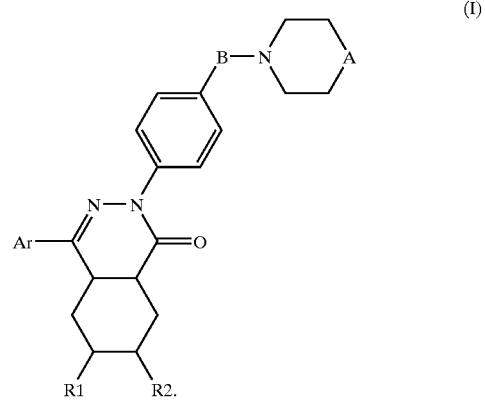

11 Claims, No Drawings

PHTHALAZINONE DERIVATIVES AS PDE4 INHIBITORS

FIELD OF APPLICATION OF THE INVENTION

The invention relates to novel phthalazinone-derivatives which are used in the pharmaceutical industry for the production of medicaments.

KNOWN TECHNICAL BACKGROUND

International Patent Applications WO98/31674, WO99/31071, WO99/31090 and WO99/47505 disclose phthalazinone derivatives having selective PDE4 inhibitory properties. In the International Patent Application WO94/12461 and in the European Patent Application EP 0 763 534 3-aryl-pyridazin-6-one and arylalkyl-diazinone derivatives are described as selective PDE4 inhibitors.

DESCRIPTION OF THE INVENTION

It has now been found that the morpholino-derivatives, which are described in greater details below, have surprising and particularly advantageous properties.
The invention thus relates to compounds of formula I

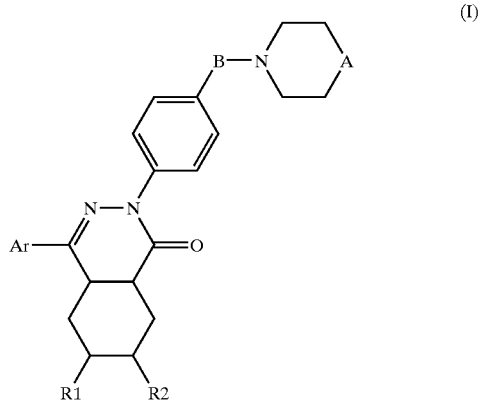

(I)

in which
R1 and R2 are both hydrogen or together form an additional bond.
Ar represents a benzene derivative of formula (a) or (b)

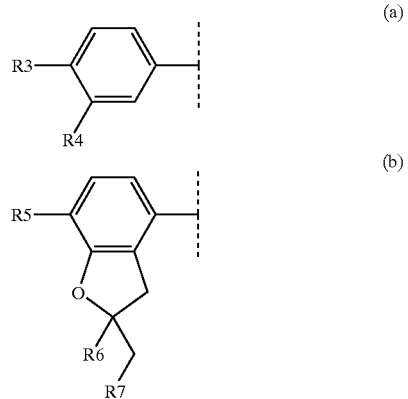

wherein
R3 is halogen, 1–4C-alkoxy, or 1–4C-alkoxy which is completely or predominantly substituted by fluorine,
R4 is halogen, 1–8C-alkoxy, 3–7C-cycloalkoxy, 3–7C-cycloalkylmethoxy, or 1–4C-alkoxy which is completely or predominantly substituted by fluorine,
R5 is halogen, 1–4C-alkoxy, 3–5C-cycloalkoxy, 3–5C-cycloalkylmethoxy, or 1–4C-alkoxy which is completely or predominantly substituted by fluorine,
R6 is 1–4C-alkyl and
R7 is hydrogen or 1–4C-alkyl,
or wherein
R6 and R7 together and with inclusion of the two carbon atoms, to which they are bonded, form a spiro-linked 5-, 6- or 7-membered hydrocarbon ring, optionally interrupted by an oxygen or sulphur atom,
B represents C(O) (carbonyl) or S(O)$_2$ (sulfonyl),
A represents O (oxygen), S (sulfur), S(O) (sulfinyl) or S(O)$_2$ (sulfonyl),
and the salts of these compounds.

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, isopropoxy, ethoxy and methoxy radicals.

1–8C-Alkoxy is a radical which, in addition to the oxygen atom, contains a straight-chain or branched alkyl radical having 1 to 8 carbon atoms. Alkoxy radicals having 1 to 8 carbon atoms which may be mentioned in this context are, for example, the octyloxy, heptyloxy, isoheptyloxy (5methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy, isopropoxy, ethoxy and methoxy radicals.

Halogen within the meaning of the present invention is bromine, chlorine and fluorine.

3–7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopenlyloxy are preferred.

3–7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopentylmethoxy are preferred.

3–5C-Cycloalkoxy stands for cyclopropyloxy, cyclobutyloxy and cyclopentyloxy.

3–5C-Cycloalkylmethoxy stands for cyclopropylmethoxy, cyclobutylmethoxy and cyclopentylmethoxy.

1–4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1–4C-alkoxy group are replaced by fluorine atoms.

As spiro-linked 5-, 6- or 7-membered hydrocarbon rings, optionally interrupted by an oxygen or sulphur atom, may be mentioned the cyclopentane, cyclohexane, cycloheptane, tetrahydrofuran, tetrahydropyran and the tetrahydrothiophen ring.

Suitable salts for compounds of the formula I are all acid addition salts. Particular mention may be made of the pharmacologically tolerable inorganic and organic acids customarily used in pharmacy. Those suitable are water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of formula I to be emphasized are those in which

R1 and R2 are both hydrogen or together form an additional bond,

Ar represents a benzene derivative of formula (a) or (b)

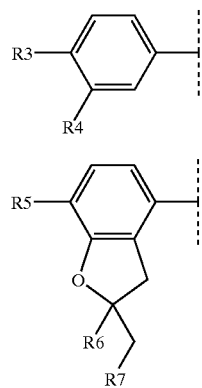

wherein
R3 is halogen, 1–4C-alkoxy, or 1–4C-alkoxy which is completely or predominantly substituted by fluorine,
R4 is halogen, 1–4C-alkoxy, 3–5C-cycloalkoxy, 3-5C-cycloalkylmethoxy or 1–4C-alkoxy which is completely or predominantly substituted by fluorine,
R5 is halogen, 1–4C-alkoxy, or 1–4C-alkoxy which is completely or predominantly substituted by fluorine,
R6 is 1–4C-alkyl and
R7 is hydrogen or 1–4C-alkyl,
or wherein
R6 and R7 together and with inclusion of the two carbon atoms, to which they are bonded, form a spiro-linked cyclopentane, cyclohexane, tetrahydrofuran or tetrahydropyran ring,
B represents C(O) (carbonyl) or S(O)$_2$ (sulfonyl),
A represents O (oxygen), S (sulfur), S(O) (sulfinyl) or S(O)$_2$ (sulfonyl),
and the salts of these compounds.

Compounds of formula I which are particularly to be emphasized are those in which
R1 and R2 together form an additional bond,
Ar represents a benzene derivative of formula (a) or (b)

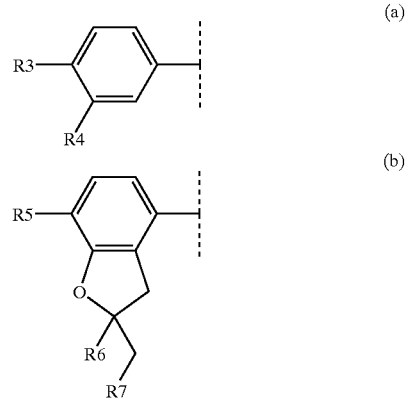

wherein
R3 is 1–2C-alkoxy or 1–2C-alkoxy which is completely or predominantly substituted by fluorine,
R4 is 1–4C-alkoxy,
R5 is 1–2C-alkoxy or 1–2C-alkoxy which is completely or predominantly substituted by fluorine,
R6 is methyl,
R7 is hydrogen,
or wherein
R6 and R7 together and with inclusion of the two carbon atoms, to which they are bonded, form a spiro-linked cyclopentane or cyclohexane ring,
B represents C(O) (carbonyl) or S(O)$_2$ (sulfonyl),
A represents O (oxygen), S (sulfur), S(O) (sulfinyl) or S(O)$_2$ (sulfonyl),
and the salts of these compounds.

Preferred compounds of formula I are those in which
R1 and R2 together form an additional bond,
Ar represents a benzene derivative of formula (a) or (b)

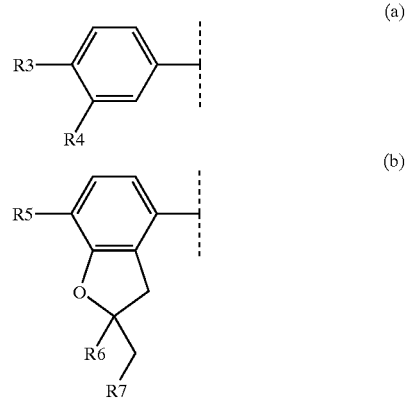

wherein
R3 is 1–2C-alkoxy or 1–2C-alkoxy which is completely or predominantly substituted by fluorine, R4 is 1–4C-alkoxy,
R5 is 1–2C-alkoxy or 1–2C-alkoxy which is completely or predominantly substituted by fluorine,
R6 is methyl,
R7 is hydrogen,
B represents C(O) (carbonyl) or S(O)$_2$ (sulfonyl),
A represents O (oxygen), S (sulfur), S(O) (sulfinyl) or S(O)$_2$ (sulfonyl),
and the salts of these compounds.

Especially preferred compounds of formula I are those in which
R1 and R2 together form an additional bond,
Ar represents a benzene derivative of formula (a) or (b)

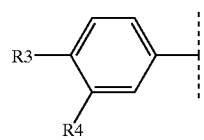
(a)

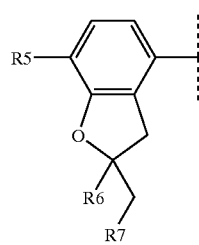
(b)

wherein
R3 is ethoxy,
R4 is ethoxy,
R5 is methoxy,
R6 is methyl,
R7 is hydrogen,
B represents C(O) (carbonyl) or S(O)$_2$ (sulfonyl),
A represents O (oxygen), S (sulfur) or S(O)$_2$ (sulfonyl),
and the salts of these compounds.

One embodiment (embodiment a) of the compounds of formula I are those in which
R1 and R2 are both hydrogen or together form an additional bond,
Ar represents a benzene derivative of formula (a) or (b)

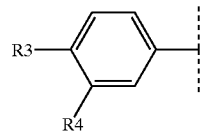
(a)

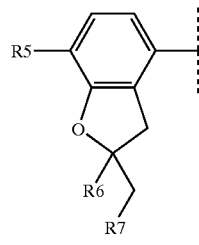
(b)

wherein
R3 is halogen, 1–4C-alkoxy, or 1–4C-alkoxy which is completely or predominantly substituted by fluorine, R4 is halogen, 1–8C-alkoxy, 3–7C-cycloalkoxy, 3–7C-cycloalkylmethoxy, or 1–4C-alkoxy which is completely or predominantly substituted by fluorine,
R5 is halogen, 1–4C-alkoxy, 3–5C-cycloalkoxy, 3–5C-cycloalkylmethoxy, or 1–4C-alkoxy which is completely or predominantly substituted by fluorine,
R6 is 1–4C-alkyl and
R7 is hydrogen or 1–4C-alkyl,
or wherein
R6 and R7 together and with inclusion of the two carbon atoms, to which they are bonded, form a spiro-linked 5-, 6- or 7-membered hydrocarbon ring, optionally interrupted by an oxygen or sulphur atom,
B represents C(O) (carbonyl),
A represents O (oxygen) or S (sulfur),
and the salts of these compounds.

Compounds of formula I of embodiment a to be emphasized are those in which
R1 and R2 are both hydrogen or together form an additional bond.
Ar represents a benzene derivative of formula (a) or (b)

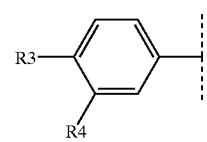
(a)

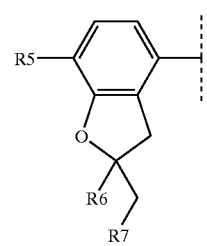
(b)

wherein
R3 is halogen, 1–4C-alkoxy, or 1–4C-alkoxy which is completely or predominantly substituted by fluorine,
R4 is halogen, 1–4C-alkoxy, 3–5C-cycloalkoxy, 3–5C-cycloalkylmethoxy or 1–4C-alkoxy which is completely or predominantly substituted by fluorine,
R5 is halogen, 1–4C-alkoxy, or 1–4C-alkoxy which is completely or predominantly substituted by fluorine,
R6 is 1–4C-alkyl and
R7 is hydrogen or 1–4C-alkyl,
or wherein
R6 and R7 together and with inclusion of the two carbon atoms, to which they are bonded, form a spiro-linked cyclopentane, cyclohexane, tetrahydrofuran or tetrahydropyran ring,
B represents C(O) (carbonyl),
A represents O (oxygen) or S (sulfur),
and the salts of these compounds.

Compounds of formula I of embodiment a which are particularly to be emphasized are those in which
R1 and R2 together form an additional bond, Ar represents a benzene derivative of formula (a) or (b)

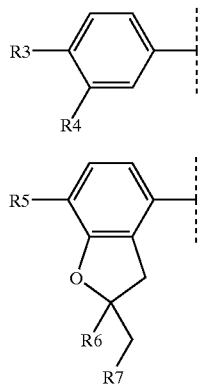

(a)

(b)

wherein
R3 is 1–2C-alkoxy or 1–2C-alkoxy which is completely or predominantly substituted by fluorine,
R4 is 1–4C-alkoxy,
R5 is 1–2C-alkoxy or 1–2C-alkoxy which is completely or predominantly substituted by fluorine,
R6 is methyl,
R7 is hydrogen,
or wherein
R6 and R7 together and with inclusion of the two carbon atoms, to which they are bonded, form a spiro-linked cyclopentane or cyclohexane ring.
B represents C(O) (carbonyl),
A represents O (oxygen) or S (sulfur),
and the salts of these compounds.

Preferred compounds of formula I of embodiment a are those in which
R1 and R2 together form an additional bond,
Ar represents a benzene derivative of formula (a) or (b)

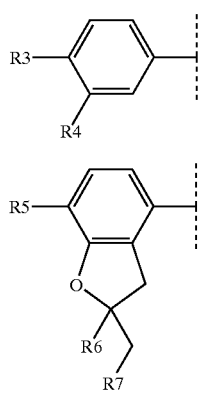

(a)

(b)

wherein
R3 is methoxy or ethoxy,
R4 is ethoxy,
R5 is methoxy,
R6 is methyl,
R7 is hydrogen,
B represents C(O) (carbonyl) and
A represents O (oxygen) or S (sulfur),
and the salts of these compounds.

The compounds of formula I are chiral compounds. Chiral centers exist in the compounds of formula I in the positions 4a and 8a. In case Ar represents a benzene derivative of formula (b) there is one further chiral center in the dihydrofuran-ring, if the substituents —R6 and —CH$_2$R7 are not identical. However, preferred are in this connection those compounds, in which the substituents —R6 and —CH$_2$R7 are identical or together and with inclusion of the two carbon atoms to which they are bonded form a spiro-connected 5-, 6- or 7-membered hydrocarbon ring.

Numbering:

(I)

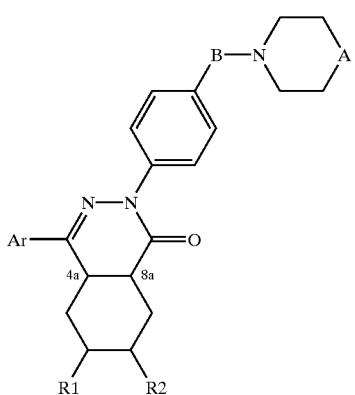

Therefore the invention includes all conceivable pure diastereomers and pure enantiomers, as well as all mixtures thereof independent from the ratio, including the racemates. Preferred are those compounds, in which the hydrogen atoms in the positions 4a and 8a are cis-configurated. Especially preferred in this connection are those compounds, in which the absolute configuration (according to the rules of Cahn, Ingold and Prelog) is S in the position 4a and R in the position 8a. Racemates can be split up into the corresponding enantiomers by methods known by a person skilled in the art. Preferably the racemic mixtures are separated into two diastereomers during the preparation with the help of an optical active separation agent on the stage of the cyclohexanecarboxylic acids or the 1,2,3,6-tetrahydrobenzoic acids (for example, starting compounds A3 and A4). As separation agents may be mentioned, for example, optical active amines such as the (+)- and (−)-forms of 1-phenylethylamine [(R)-(+)-1-phenylethylamine=(R)-(+)-α-methylbenzylamine or (S)-(−)-1-phanylethylamine=(S)-(−)-α-methylbenzylamine) and ephedrine, the optical active alkaloids quinine, cinchonine, cinchonidine and brucine.

The compound according to the invention can, for example, be prepared as described in Reaction Scheme 1. In a first step the cyclohexanecarboxylic or 1,2,3,6-tetrahydrobenzoic acids are reacted with 4-hydrazinobenzoic acid or 4-hydrazinobenzene sulfonic acid. The resulting compounds are activated, for example, with phosphorus pentachloride or oxalyl chloride and then treated with morpholine or thiomorpholine.

Oxidised thiomorpholine derivatives of formula I can be prepared for example starting from the corresponding thiomorpholine derivatives of formula I using standard oxidation methods, preferably m-chloroperbenzoic acid in dichloromethane at 0° C.

Reaction Scheme 1:

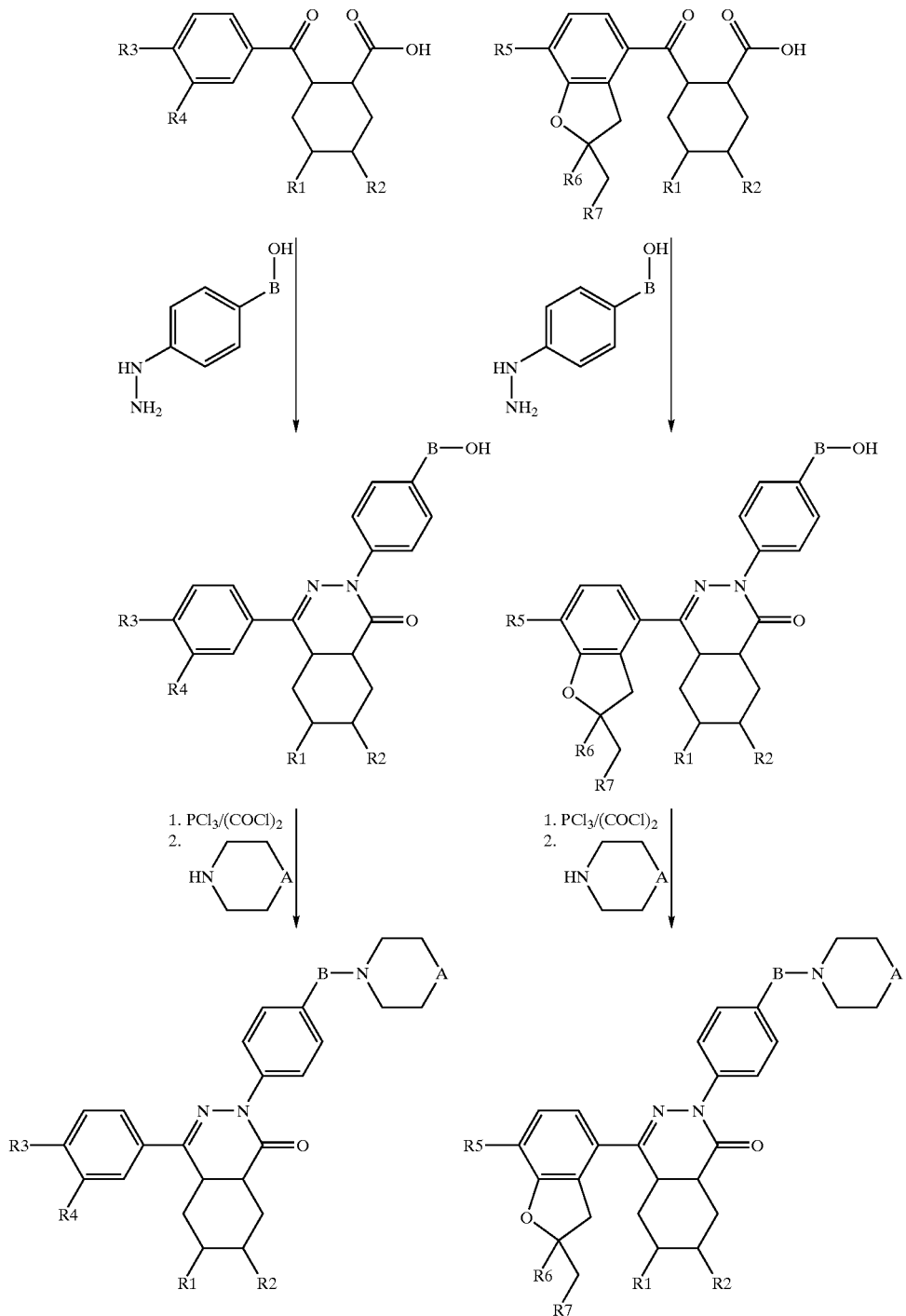

Suitably, the conversions are carried out analogous to methods which are familiar per so to the person skilled in the art, for example, in the manner which is described in the following examples.

The preparation of the cyclohexanecarboxylic acids and 1,3,5,6-tetrahydrobenzoic acids is described, for example, in WO98/31674 and WO99/31090.

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula I, of which the preparation is explicitly not described, can be prepared in an analogous way or in a way which is known by a person skilled in the art using customary preparation methods.

The compounds, which are mentioned in the examples as well as their salts are preferred compounds of the invention.

EXAMPLES

Final Products 1. (cis)-4-(3,4-Diethoxyphenyl)-2-[4-(N-morpholinocarbonyl)phenyl]-4a,5,8,8a-tetrahydro-2H-phthalazin-1-one A solution of 2.0 g of starting compound A1 and 2.0 g of phosphorus pentachloride in 20 ml of dichloromethane is stirred, under a flow of nitrogen, for 1 hour, after which this solution is slowly added to a solution of 1.0 g of morpholine in 50 ml of pyridine. After stirring this mixture for 18 hours, the mixture is evaporated. The residue is dissolved in ethyl acetate and this solution is washed successively with 1N hydrochloric acid and aqueous sodium carbonate. After drying over magnesium sulfate and evaporating the solvent, the compound is crystallised from a mixture of ethyl acetate and petroleum ether (60–80° C.). M. p. 144–145° C.

2. (cis)-4-(2,3-Dihydro-2,2-dimethyl-7-methoxybenzofuran-4-yl)-2-[4-(N-morpholinocarbonyl)-phenyl]-4a,5,8,8a-tetrahydro-2H-phthalazin-1-one Prepared as described for compound 1 from 10.0 g of starting compound A2 and 5.0 g of morpholine in 100 ml of pyridine. Crystallised first from diethyl ether and then from methanol. Yield: 8.9 g. M. p. 197–199° C.

3. (cis)-4-(3,4-Diethoxyphenyl)-2-[4-(1-thiomorpholin-4-ylcarbonyl)phenyl]-4a,5,8,8a-tetrahydro-2H-phthalazin-1-one A mixture of 1.5 g starting compound A1 and 10 ml of oxalyl chloride is stirred for 2 h at room temperature after which the mixture is evaporated. The residue is dissolved in 10 ml of dichloromethane. To this solution, a mixture of 0.4 g of thiomorpholine and 5 ml of triethylamine is added and the resulting mixture is stirred for 18 h at room temperature. After diluting the reaction mixture with 100 ml of dichloromethane, this solution is washed successively with 1N hydrochloric acid and aqueous sodium carbonate. The dichloromethane layer is dried over magnesium sulfate and evaporated. The compound is crystallised from methanol. Yield: 0.8 g. M. p. 104–106° C.

4. (cis)-4-(3,4-Diethoxyphenyl)-2-[4-(N-morpholinosulfonyl)phenyl]-4a,5,8,8a-tetrahydro-2H-phthalazin-1-one Prepared as described for compound 1 starting from compound A5 and morpholine. Crystallised from methanol. M. p. 160–161° C.

5. (cis)-4-(2,3-Dihydro-2,2-dimethyl-7-methoxybenzofuran-4-yl)-2-[4(N-morpholinosulfonyl) phenyl]-4a,5,8,8a-tetrahydro-2H-phthalazin-1-one Prepared as described for compound 1 starting from compound A6 and morpholine. Purified by chromatography [ethyl acetate/petroleum ether(60–80° C.) 1:1]. Crystallised from diethyl ether. M. p. 217–218° C.

6. (cis)-4-(3,4-Diethoxyphenyl)-2-[4-(1,1-dioxothiomorpholin-4-ylcarbonyl)phenyl]-4a,5,8,8a-tetrahydro-2H-phthalazin-1-one 3.2 mmol of m-chloroperbenzoic acid are added slowly to a solution of 1.6 mmol of example 3 in 50 ml of dichloromethane at 0° C. After complete addition, the solution is washed with aqueous sodium carbonate, dried over magnesium sulfate and evaporated. Crystallised from methanol. M. p. 186–187° C.

Starting Compounds

A1. (cis)-4-(4-(3,4-Diethoxyphenyl)-1-oxo-4a,5,8,8a-tetrahydro-1H-phthalazin-2-yl)benzoic acid A solution of 8 g of starting compound A4 and 8 g of 4-hydrazinobenzoic acid in a mixture of 100 ml of 1-propanol and 5 ml of triethylamine is refluxed for 18 h. After evaporating the solvent, the residue is partitioned between aqueous sodium carbonate and ethyl acetate. The organic layer is dried over magnesium sulfate and evaporated. The residue is purified by chromatography.

A2. (cis)-4-{(2,3-Dihydro-2,2-dimethyl-7-methoxybenzofuranyl)-1-oxo-4a,5,8,8a-tetrahydro-phthalazin-2-yl}benzoic acid A solution of starting compound A3 10 g of 4-hydrazinobenzoic acid and 3 g of pyridine hydrochloride in 50 ml of pyridine is refluxed for 18 h. After evaporating this solution, the residue is dissolved in ethyl acetate and washed 3 times with 1N hydrochloric acid. The solution is then dried over magnesium sulfate and evaporated. The compound is crystallised from diethyl ether. Yield: 12 g. M. p. 212–214° C.

A3. (cis)-2-(2,3-Dihydro-2,2-dimethyl-7-methoxybenzofuran-4-carbonyl)-1,2,3,6-tetrahydro-benzoic acid Prepared as Described in WO99/31090.

A4. (cis)-2-(3,4-Diethoxybenzoyl)-1,2,3,6-tetrahydrobenzoic acid

Prepared analogously as described in WO98/31674.

A5. (cis)-4-{4-(3,4-Diethoxyphenyl)-1-oxo-4a,5,8,8a-tetrahydro-1H-phthalazin-2-yl}benzenesulfonic acid A solution of 16 mmol of starting compound A4, 16 mmol of 4-hydrazino benzene sulfonic acid and 5 ml of triethyl amine in 100 ml of 1-propanol is refluxed for 6 h. After evaporating the residue is dissolved in 100 ml of acetic acid and refluxed for 2 h. After evaporating the residue is partitioned between 1N hydrochloric acid and ethyl acetate, The organic layer is dried over magnesium sulfate and evaporated. Crystallisation from diethyl ether. M. p. 65–69° C.

A6. (cis)-4-{(2,3-Dihydro-2,2-dimethyl-7-methoxybenzofuranyl)-1-oxo-4a,5,5,8a-tetrahydro-phthalazin-2-yl}benzenesulfonic acid Prepared from starting compound A3 and 4-hydrazino benzene sulfonic acid as described for starting compound A5. M. p. 129–130° C.

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis. osteoarthritis and other arthritic conditions), disorders of the immune system (AIDS, multiple sclerosis), graft versus host reaction, allograft rejections, types of shock [septic shock, endotoxin shock, gram-negative, sepsis, toxic shock syndrome and ARDS (adult respiratory distress syndrome)] and also generalized inflammations in the gastrointestinal region Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The medicaments are prepared by processes which are known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled In the art is familiar with auxiliaries which are suitable for the desired pharmaceutical formulations on account of his expert knowledge. In addition to solvents, gel formers, ointment bases and other active compound excipients, for example antioxidants, dispersants, emulsifiers, preservatives, solubilizers or permeation promoters, can be used.

For the treatment of disorders of the respiratory tract, the compounds according to the invention are preferably also administered by inhalation. To do this, these are either administered directly as a powder (preferably in micronized form) or by atomizing solutions or suspensions which contain them. With respect to the preparations and administration forms, reference is made, for example, to the details in European Patent 163 965.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customarly between 0.1 and 3 mg per day. The customary dose in the case of systemic therapy (p.o. or i.v.) is between 0.03 and 3 mg/kg per day.

Biological Investigations

In the investigation of PDE 4 inhibition on the cellular plane, the activation of inflammatory cells is ascribed particular importance. An example is FMLP (N-formyl-methionyl-leucyl-phenylalanine) induced superoxide production of neutrophilic granulocytes, which can be measured as luminol-amplified chemiluminescence. (Mc Phail L C, Strum S L, Leone P A and Sozzani S. The neutrophil respiratory burst mechanism. In "Immunology Series" 57: 47–76, 1992; ed. Coffey R G (Marcel Decker, Inc., New York-Basel-Hong Kong)).

Substances which inhibit chemiluminescence and cytokine secretion and the secretion of proinflammatory mediators on inflammatory cells, in particular neutrophilic and eosinophilic granulocytes, T-lympho-cytes, monocytes and macrophages are those which inhibit PDE 4. This isoenzyme of the phosphodiesterase families is particularly represented in granulocytes. Its inhibition leads to an increase in the intracellular cyclic AMP concentration and thus to the inhibition of cellular activation. PDE 4 inhibition by the substances according to the invention is thus a central indicator for the suppression of inflammatory processes. (Giembycz M A, Could isoenzyme-selective phosphodiesterase inhibitors render bronchodilatory therapy redundant in the treatment of bronchial asthma?. Biochem Pharmacol 43: 2041–2051, 1992; Torphy T J et al., Phosphodiesterase inhibitors: new opportunities for treatment of asthma. Thorax 46: 512–523, 1991; Schudt C et al., Zardaverine: a cyclic AMP PDE 3/4 inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and Ca; Naunyn-Schmiedebargs Arch Pharmacol 344; 682–690, 1991; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE3/4-Inhibitors. In "Phosphodiesterase Inhibitors", 147–160, "The Handbook of Immunopharmacology", Academic Press, 1996.

Inhibition f PDE 4 Activity

Methodology

The activity test was carried out according to the method of Bauer and Schwabe, which was adapted to microtitre plates (Naunyn-Schmiederberg's Arch. Pharmacol. 311, 193–198. 1980). In this test, the PDE reaction is carried out in the first step. In a second step, the resultant 5'-nucleotide is cleaved to the uncharged nucleoside by a snake venom 5'-nucleotidase from Crotalus Atrox. In the third step, the nucleoside is separated from the remaining charged substrate on ion exchange columns. The columns are eluted directly into minivials using 2 ml of 30 mM ammonium formate (pH 6.0), to which a further 2 ml or scintillation fluid is added for counting.

The inhibitory values determined for the compounds according to the invention follow from the following table A, in which the numbers of the compounds correspond to the numbers of the examples.

TABLE A

Inhibition of PDE4 activity [measured as $-\log IC_{50}$ (mol/l)]

| compound | $-\log IC_{50}$ |
|---|---|
| 1 | 7.99 |
| 2 | 8.77 |
| 3 | 7.82 |
| 4 | 9.22 |

TABLE A-continued

Inhibition of PDE4 activity [measured as $-\log IC_{50}$ (mol/l)]

| compound | $-\log IC_{50}$ |
|---|---|
| 5 | 9.71 |
| 6 | 7.81 |

What is claimed is:

1. A compound of formula I

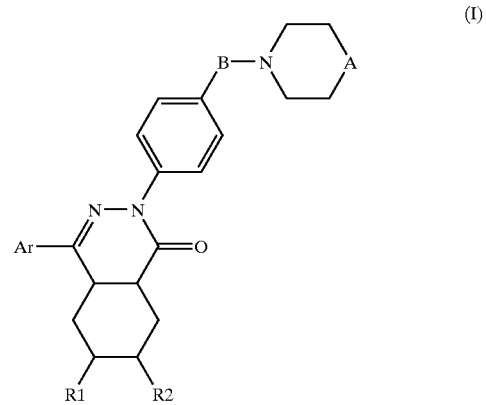

in which

R1 and R2 are both hydrogen or together form an additional bond,

Ar represents a benzene derivative of formula (a) or (b)

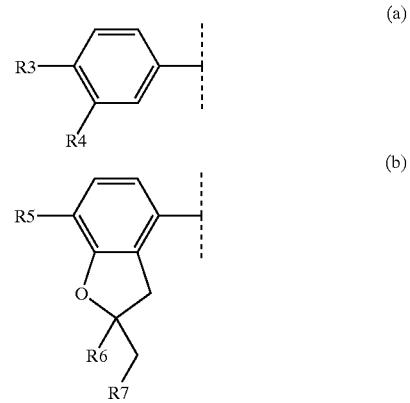

wherein

R3 is halogen, 1–4C-alkoxy, or 1–4C-alkoxy which is completely or predominantly substituted by fluorine, R4 is halogen, 1–8C-alkoxy, 3–7C-cycloalkoxy, 3–7C-cycloalkylmethoxy, or 1–4C-alkoxy which is completely or predominantly substituted by fluorine, R5 is halogen, 1–4C-alkoxy, 3–5C-cycloalkoxy, 3–5C-cycloalkylmethoxy, or 1–4C-alkoxy which is completely or predominantly substituted by fluorine, R6 is 1–4C-alkyl and R7 is hydrogen or 1–4C-alkyl, or wherein R6 and R7 together and with inclusion of the two carbon atoms, to which they are bonded, form a spiro-linked 5-, 6- or 7-membered hydrocarbon ring, optionally interrupted by an oxygen or sulfur atom, B represents C(O) (carbonyl) or S(O)$_2$ (sulfonyl), A represents O(oxygen), S (sulfur), S(O) (sulfinyl) or S(O)$_2$ (sulfonyl), or a salt thereof.

2. A compound of formula I according to claim 1 in which

R1 and R2 are both hydrogen or together form an additional bond,

Ar represents a benzene derivative of formula (a) or (b)

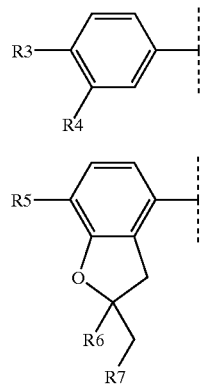

wherein

R3 is halogen, 1–4C-alkoxy, or 1–4C-alkoxy which is completely or predominantly substituted by fluorine, R4 is halogen, 1–4C-alkoxy, 3–5C-cycloalkoxy, 3–5C-cycloalkylmethoxy, or 1–4C-alkoxy which is completely or predominantly substituted by fluorine, R5 is halogen, 1–4C-alkoxy, or 1–4C-alkoxy which is completely or predominantly substituted by fluorine, R6 is 1–4C-alkyl and R7 is hydrogen or 1–4C-alkyl, or wherein R6 and R7 together and with inclusion of the two carbon atoms, to which they are bonded, form a spiro-linked cyclopentane, cyclohexane, tetrahydrofuran or tetrahydropyran ring, B represents C(O) (carbonyl) or S(O)$_2$ (sulfonyl), A represents O(oxygen), S (sulfur), S(O) (sulfinyl) or S(O)$_2$ (sulfonyl), or a salt thereof.

3. A compound of formula I according to claim 1 in which

R1 and R2 together form an additional bond,

Ar represents a benzene derivative of formula (a) or (b)

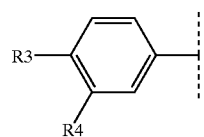

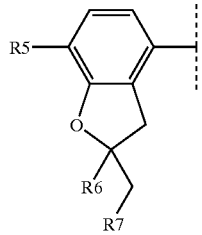

wherein

R3 is 1–2C-alkoxy or 1–2C-alkoxy which is completely or predominantly substituted by fluorine, R4 is 1–4C-alkoxy, R5 is 1–2C-alkoxy or 1–2C-alkoxy which is completely or predominantly substituted by fluorine, R6 is methyl, R7 is hydrogen, B represents C(O) (carbonyl) or S(O)$_2$ (sulfonyl), A represents O (oxygen), S (sulfur), S(O) (sulfinyl) or S(O)$_2$ (sulfonyl), or a salt thereof.

4. A compound of formula I according to claim 1 in which

R1 and R2 together form an additional bond,

Ar represents a benzene derivative of formula (a) or (b)

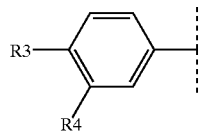

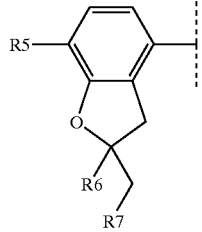

wherein

R3 is ethoxy,

R4 is ethoxy,

R5 is methoxy,

R6 is methyl,

R7 is hydrogen,

B represents C(O) (carbonyl) or S(O)$_2$ (sulfonyl),

A represents O(oxygen), S (sulfur) or S(O)$_2$ (sulfonyl), or a salt thereof.

5. A compound of formula I according to claim 1 in which

R1 and R2 are both hydrogen or together form an additional bond,

Ar represents a benzene derivative of formula (a) or (b)

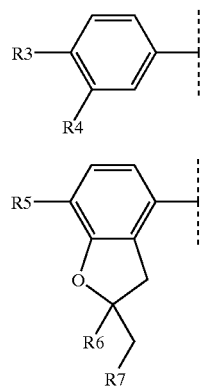

wherein
R3 is halogen, 1–4C-alkoxy, or 1–4C-alkoxy which is completely or predominantly substituted by fluorine,
R4 is halogen, 1–8C-alkoxy, 3–7C-cycloalkoxy, 3–7C-cycloalkylmethoxy, or 1–4C-alkoxy which is completely or predominantly substituted by fluorine,
R5 is halogen, 1–4C-alkoxy, 3–5C-cycloalkoxy, 3–5C-cycloalkylmethoxy, or 1–4C-alkoxy which is completely or predominantly substituted by fluorine,
R6 is 1–4C-alkyl and
R7 is hydrogen or 1–4C-alkyl,
or wherein
R6 and R7 together and with inclusion of the two carbon atoms, to which they are bonded, form a spiro-linked 5-, 6- or 7-membered hydrocarbon ring, optionally interrupted by an oxygen or sulfur atom,
B represents C(O) (carbonyl),
A represents O(oxygen) or S (sulfur),
or a salt thereof.

6. A compound of formula I according to claim 1 in which
R1 and R2 together form an additional bond,
Ar represents a benzene derivative of formula (a) or (b)

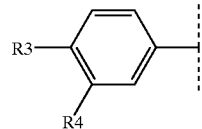

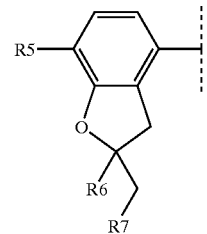

wherein

R3 is methoxy or ethoxy,
R4 is ethoxy,
R5 is methoxy,
R6 is methyl,
R7 is hydrogen,
B represents C(O) (carbonyl) and
A represents O (oxygen) or S (sulfur),
or a salt thereof.

7. A compound of formula I according to claim 1, wherein the hydrogen atoms in positions 4a and 8a are cis-configurated.

8. A compound of formula I according to claim 1, wherein the absolute configuration is S in position 4a and R in position 8a.

9. A pharmaceutical composition comprising one or more compounds of formula I according to claim 1 together with pharmaceutically acceptable auxiliaries and/or carrier materials.

10. A method for treating asthma and/or COPD in a patient comprising administering to a patient in need thereof a therapeutically effective amount of a compound of formula I as claimed in claim 1.

11. A method for treating asthma, COPD, rheumatoid arthritis, dermatoses or Crohn's disease in a patient comprising administering to a patient in need thereof a therapeutically effective amount of a compound of formula I as claimed in claim 1.

* * * * *